US005670371A

United States Patent [19]
Aviv et al.

[11] Patent Number: 5,670,371
[45] Date of Patent: Sep. 23, 1997

[54] BACTERIAL EXPRESSION OF SUPEROXIDE DISMUTASE

[75] Inventors: Haim Aviv; Marian Gorecki; Avigdor Levanon, all of Rehovot; Amos Oppenheim, Jerusalem; Jacob Hartman, Holon, all of Israel

[73] Assignee: Bio-Technology General Corp., Iselin, N.J.

[21] Appl. No.: 459,356

[22] Filed: Jun. 2, 1995

Related U.S. Application Data

[63] Continuation of Ser. No. 291,838, Aug. 17, 1994, which is a continuation of Ser. No. 92,759, Jul. 16, 1993, abandoned, which is a continuation of Ser. No. 790,773, Nov. 12, 1991, abandoned, which is a continuation of Ser. No. 355,569, May 23, 1989, abandoned, which is a continuation of Ser. No. 751,791, Jul. 3, 1985, abandoned, which is a continuation-in-part of Ser. No. 514,188, Jul. 15, 1983, abandoned.

[30] Foreign Application Priority Data

Jul. 3, 1984 [EP] European Pat. Off. ............. 84107717

[51] Int. Cl.$^6$ .................................................. C12N 15/73
[52] U.S. Cl. .............................. 435/320.1; 435/69.1
[58] Field of Search ............................ 435/69.1, 91.1, 435/172.3, 320.1, 252.3–252.35, 189; 935/9, 38, 73; 536/23.2, 23.5

[56] References Cited

U.S. PATENT DOCUMENTS

| 4,356,270 | 10/1982 | Itakura . | |
|---|---|---|---|
| 4,366,246 | 12/1982 | Riggs . | |
| 4,578,355 | 3/1986 | Rosenberg | 435/172.3 |
| 4,742,004 | 5/1988 | Hartman et al. | 435/189 |
| 4,831,120 | 5/1989 | Aviv et al. | 530/399 |
| 4,997,916 | 3/1991 | Aviv et al. | 530/399 |
| 5,143,836 | 9/1992 | Hartman et al. | 435/189 |
| 5,162,217 | 11/1992 | Hartman et al. | 435/189 |
| 5,256,546 | 10/1993 | Aviv et al. | 435/69.4 |

FOREIGN PATENT DOCUMENTS

| 0041767 | 12/1981 | European Pat. Off. . |
| 0060045 | 9/1982 | European Pat. Off. . |
| 0070632 | 1/1983 | European Pat. Off. . |
| 0131843 | 1/1984 | European Pat. Off. . |
| 0114777 | 8/1984 | European Pat. Off. . |
| 1568047 | 5/1980 | United Kingdom . |

OTHER PUBLICATIONS

Rosenberg et al, Methods in Enzymology 101: 123 (1983).
Bernard, et al., Gene, 5:59–76 (1979).
Derom, et al., Gene, 17:45–54 (1982).
Maniatis, et al., Molecular Cloning: A Laboratory Manual. Cold Spring Harbor Laboratory, Cold Spring Harbor, New York, pp. 406–409 and 418–421 (1982).

Derynck, et al., Nature, vol. 287:193 (Sep. 18, 1980).

Liy, et al., Critical Review in Biochemistry, vol. 15: Issue 1 pp. 1–23 (1983).

Oppenheim, et al., J. Mol. Bio., 158:327–346 (1982).

Shatzman, et al., Chemical Abstracts, vol. 100:186561v (1984).

Shatzman and Rosenberg, Miami Symposium, (1982).

Shimatake and Rosenberg, Nature, vol. 292: 128 (Jul. 9, 1981).

Liao, et al., Master Thesis, National Taiwan University–Research Institute of Agricultural Chemistry (Jun., 1981) pp. 80–82.

Lieman–Hurwitz, et al., Proc. Natl. Acad. Sci, vol. 79, pp. 2808–2811 (May 1981).

Lieman–Hurwitz, et al., Biochemistry International, vol. 3, No. 2:107 (Aug. 1981).

*Primary Examiner*—James Martinell
*Attorney, Agent, or Firm*—John P. White

[57] ABSTRACT

A plasmid for the production of superoxide dismutase or an analog thereof which upon introduction into a suitable bacterial host containing the thermolabile repressor $C_I$ renders the host cell capable, upon increasing the temperature of the host cell to a temperature at which the repressor is destroyed, of effecting expression of DNA encoding superoxide dismutase and production of superoxide dismutase. The plasmid is a double-stranded DNA molecule which includes in 5' to 3' order the following: a DNA sequence which contains the promoter and operator $P_LO_L$ from lambda bacteriophage; the N utilization site for binding antiterminator N protein produced by the host cell; a DNA sequence which contains a ribosomal binding site for rendering the mRNA of the gene encoding superoxide dismutase capable of binding to ribosomes within the host cell; an ATG initiation codon; a restriction enzyme site for inserting the gene encoding superoxide dismutase into the plasmid in phase with the ATG initiation codon; a gene encoding superoxide dismutase; and additionally a DNA sequence which contains an origin of replication from a bacterial plasmid capable of autonomous replication in the host cell and a DNA sequence which contains a gene associated with a selectable or identifiable trait which is manifested when the plasmid is present in the host cell.

2 Claims, 7 Drawing Sheets

FIG. 6

```
          1   2   3   4   5   6   7   8   9   10  11  12  13  14  15  16  17  18  19  20  21  22  23  24  25  26
          ALA THR LYS ALA VAL CYS VAL LEU LYS GLY ASP GLY PRO VAL GLN GLY ILE ILE ASN PHE GLU GLN LYS GLU SER ASN
G32 ATG,GCG,ACG,AAG,GCC,GTG,TGC,GTG,CTG,AAG,GGC,GAC,GGC,CCA,GTG,CAG,GGC,ATC,ATC,AAT,TTC,GAG,CAG,AAG,GAA,AGT,AAT,
                         40                      50                      60                      70                      80                      90                     100                     110

27  28  29  30  31  32  33  34  35  36  37  38  39  40  41  42  43  44  45  46  47  48  49  50  51  52  53
  GLY PRO VAL LYS VAL TRP GLY VAL SER ILE LYS GLY LEU THR GLU GLY LEU HIS GLY PHE HIS VAL HIS GLU PHE GLY ASP ASN
  GGA,CCA,GTG,AAG,GTG,TGG,GGA,AGC,AGT,ATA,AAA,GGA,CTG,ACT,GAA,GGC,CTG,CAT,GGA,TTC,CAT,GTT,CAT,GAG,TTT,GGA,GAT,AAT,
         120                     130                     140                     150                     160                     170                     180                     190

54  55  56  57  58  59  60  61  62  63  64  65  66  67  68  69  70  71  72  73  74  75  76  77  78  79  80
  THR ALA GLY CYS THR SER ALA GLY PRO HIS PHE ASN PRO LEU SER ARG LYS HIS GLY PRO LYS HIS GLY GLU ARG HIS
  ACG,GCA,GGC,TGT,ACC,AGT,GCA,GGT,CCT,CAC,TTT,AAT,CCT,CTA,TCC,AGA,AAA,CAC,GGT,CCA,AAG,CAT,GAA,GAG,AGG,CAT,
         200                     210                     220                     230                     240                     250                     260                     270

81  82  83  84  85  86  87  88  89  90  91  92  93  94  95  96  97  98  99  100 101 102 103 104 105 106 107
  VAL GLY ASP LEU GLY ASN VAL THR ALA ASP LYS ASP GLY VAL ALA ASP VAL SER ILE GLU ASP SER VAL ILE SER LEU SER
  GTT,GGA,GAC,TTG,GGC,AAT,GTG,ACT,GCT,GAC,AAA,GAT,GGT,GTG,GCC,GAT,GTG,TCT,ATT,GAA,GAT,TCT,GTG,ATC,TCA,CTC,TCA,
         280                     290                     300                     310                     320                     330                     340                     350

108 109 110 111 112 113 114 115 116 117 118 119 120 121 122 123 124 125 126 127 128 129 130 131 132 133 134
  GLY ASP HIS CYS ILE ILE GLY ARG THR LEU VAL VAL HIS GLU LYS ALA ASP ASP LEU GLY LYS GLY GLY ASN GLU GLU SER
  GGA,GAC,CAT,TGC,ATC,ATT,GGG,CGC,ACA,CTG,GTC,GTC,CAT,GAA,AAA,GCA,GAC,GAC,TTG,GGC,AAA,GGT,GGC,AAT,GAA,GAA,AGT,
         360                     370                     380                     390                     400                     410                     420                     430

135 136 137 138 139 140 141 142 143 144 145 146 147 148 149 150 151 152 153
  THR LYS THR GLY ASN ALA GLY SER ARG LEU ALA CYS GLY VAL ILE GLY ILE ALA GLN STOP
  ACA,AAG,ACA,GGA,AAC,GCT,GGA,AGT,CGT,TTG,GCT,TGT,GGT,GTA,ATT,GGG,ATC,GCC,CAA, TAAACATTCCCCTTGGATGTAGTCTGAG
         440                     450                     460                     470                     480                     490                     500                     510                     520

GCCCTTAACTCATCTGTTATCCTGCTAGCTGTGAGAAATGTATCTGATAAACATTAAACACTGT AATCTTAAAAAAAAAC17
         530                     540                     550                     560                     570                     580                     590                     600
```

BACTERIAL EXPRESSION OF SUPEROXIDE DISMUTASE

This application is a continuation of U.S. Ser. No. 08/291,838, filed Aug. 17, 1994; which is a continuation of U.S. Ser. No. 08/092,759, filed Jul. 16, 1993, now abandoned; which is a continuation of U.S. Ser. No. 07/790,773, filed Nov. 12, 1991, now abandoned; which was a continuation of U.S. Ser. No. 07/355,569, filed May 23, 1989, now abandoned; which was a continuation of U.S. Ser. No. 06/751,791, filed Jul. 3, 1985, now abandoned; which was a continuation-in-part of U.S. Ser. No. 06/514,188, filed Jul. 15, 1983, abandoned.

BACKGROUND OF THE INVENTION

One aspect of genetic engineering involves the insertion of foreign DNA sequences derived from eukaryotic sources into *Escherichia coil* or other microorganisms. A further refinement of genetic engineering concerns inducing the resulting microorganism to produce polypeptides encoded by the foreign DNA. Production of polypeptides can be considered a two-step process, with each step including numerous substeps. The two steps are transcription and translation. To produce a polypeptide efficiently and in quantity both steps of the process must be efficient. Transcription is the production of mRNA from the gene (DNA). Translation is the production of polypeptide from the mRNA.

A critical substep of the transcription process is initiation, that is, the binding of RNA polymerase to a promoter-operator region. The sequence of deoxyribonucleotide bases which make up the promoter region may vary and thereby effect the relative efficiency of the promoter. The efficiency depends on the affinity of the RNA polymerase for the promoter.

The efficiency of translation is affected by the stability of the mRNA. Increased stability of the mRNA permits improved translation. Although the exact determinants of mRNA stability are not precisely known, it is known that mRNA secondary structure as determined by the sequence of its bases has a role in stability.

The initial substep of translation involves binding of the ribosome to a base sequence on the mRNA known as the Shine-Dalgarno sequence or the ribosomal binding site (RBS). The synthesis of polypeptides begins when the ribosome migrates along the mRNA to the AUG start codon for translation. Generally these codons are found approximately 10 bases "downstream" from the Shine-Dalgarno site. Factors which increase the efficiency of translation include those which enhance binding of the ribosomes to the Shine-Dalgarno site. It has been shown that the secondary structure of the mRNA in the region of the Shine-Dalgarno sequence and the AUG codon and the distance between the Shine-Dalgarno sequence and the AUG codon each play a critical role in determining the efficiency of translation. Other factors which affect the efficiency of translation are premature termination and attenuation. Efficiency of translation can be improved by removing the attenuation sites.

A difficulty encountered in attempts to produce high amounts of eukaryotic polypeptides in bacterial cells involves the inability of cells producing large amounts of mRNA to grow efficiently. This difficulty can be eliminated by preventing transcription by a process known as repression. In repression genes are switched off due to the action of a protein inhibitor (repressor protein) which prevents transcription by binding to the operator region. After microorganisms have grown to desired cell densities, the repressed genes are activated by destruction of the repressor or by addition of molecules known as inducers which overcome the effect of the repressor.

Numerous reports may be found in the literature concerning the cloning of eucaryotic genes in plasmids containing the $P_L$ promoter from λ bacteriophage. (Bernard, H. V. et al., Gene (1979) 5, 59; Derom, C. et al., Gene (1982) 17, 45; Gheysen, D. et al., Gene (1982) 17, 55; Hedgpeth, J. et al., Mol. Gen. Genet. (1978) 163, 197; Remaut, E. et al., (1981) Gene 15, 81; and Derynck, R., et al., Nature (1980) 287, 193. In addition, European Patent Application No. 041,767, published Dec. 16, 1981 describes expression vectors containing the $P_L$ promoter from λ bacteriophage. However, none of these references describe the use of the $C_{II}$ ribosomal binding site.

The use of a vector containing the $P_L$ promoter from λ bacteriophage and the $C_{II}$ ribosomal binding site has been described. (Oppenheim, A. B. et al., J. Mol. Biol. (1982) 158, 327 and Shimatake, H. and Rosenberg, M., Nature (1981) 292, 128.) These publications describe the production of increased levels of $C_{II}$ protein but do not involve or describe the production of eucaryotic proteins.

In 1982 Shatzman and Rosenberg presented a poster at the 14th Miami Winter Symposium (Shatzman, A. R. and Rosenberg, M., 14 Miami Winter Symposium, abstract p98 [1982]). This abstract provides a non-enabling disclosure of the use of a vector containing $P_L$ from λ bacteriophage, Nut and the $C_{II}$ ribosomal binding site to synthesize a "eucaryotic" polypeptide (SV40 small T antigen is actually not a eucaryotic polypeptide but a vital protein) in an amount greater than 5% of the cell protein in an unnamed bacterial host. The operator used is not defined. Neither an origin of replication nor a gene for a selectable phenotype is identified. This system with which the vector is used is described as including certain host lysogens into which the vector can be stably transformed. The present invention in one embodiment, i.e., pMG100, may have certain similarities to this vector. However, it is not transformed into a host lysogen, but rather into-suitable *E. coli* host strains which contain the thermolabile repressor $C_I$ and the N gene but from which the rest of the lysogen has been removed. Moreover, it has been employed to produce bGH and hGH analogs in amounts in excess of 20% of total cell protein.

In addition, in other embodiments of this invention ribosomal binding sites which differ from $C_{II}$ are employed. Also, in the presently most preferred vectors, pND5 and its derivatives, nonessential sequences have been removed to create a vector permitting polypeptide production in amounts which are more than 10% greater than those obtained with pMG100.

Recently, applicants have learned of the existence of a pending U.S. patent application in the name of M. Rosenberg filed under Ser. No. 457,352 by the National Institutes of Health, Dept. of Health and Human Services, U.S.A. Portions of this application have been obtained from the National Technical Information Service, U.S. Dept. of Commerce. However, the claims are not available and are maintained in confidence. The available portions of the application have been reviewed. This disclosure is not enabling. It indicates that the host is important (p8, line 17) but fails to identify any suitable host. It further depends upon the use of a λ mutant which is not specified (p4, line 20). It indicates that the host contains lysogens (p8, line 18) unlike the present invention in which the host is not lysogenic. It mentions cloning and expression of a eucaryotic gene, monkey metallothionein gene, (p7, line 18) but does not provide details. It specifies that neither the sequence nor the position of any nucleotide in the $C_{II}$ ribosomal binding region has been altered. (p3, line 27)

In the present invention such alteration is possible.

No disclosure is present in the art concerning: successful expression with a $P_L$-$C_{II}$ containing vector system of bovine or human growth hormones or superoxide dismutase; production of bGH, hGH or SOD analogs having biological activity; compositions containing such analogs or uses of them; or induction methods for achieving polypeptide production in amounts greater than 20% of the total protein produced by the host.

The only disclosure in the art concerning production of bGH analogs by hosts transformed with genetically engineered vectors involves the use of the Trp promoter to produce a bGH analog having the amino acid Met at the N-terminus of the phenylalanine form of natural bGH (Seeburg, P. H. et al., DNA (1983) 2, 37.

The only disclosure in the art concerning production of hGH analogs by hosts transformed with genetically engineered vectors involves the use of the Lac and Trp promoters to produce an analog of hGH having the amino acid Met at the N-terminus of the natural hGH. (Goedell, D. V. et al., Nature (1979) 281, 544)

There is no disclosure in the prior art concerning the production of superoxide dismutase (SOD) or analogs thereof by hosts transformed with genetically engineered plasmids. There is also no disclosure in the prior art of bacterially produced superoxide dismutase. Moreover, the gene encoding human cytoplasmic superoxide dismutase has only recently been cloned and a cDNA prepared. See LiemanHurwitz, et al., Proc. Natl. Acad. Sci. USA 79, 2808–2811 (1982). The complete sequence of the cloned DNA has been determined. See Proc. Natl. Acad. Sci. USA 80, 5465–5469 (1983). See also pending U.S. application Ser. No. 489,786 filed Apr. 29, 1983. Until the present invention, it has been unknown whether SOD could be produced in bacteria and whether, if so produced, the SOD would be active. In view of prior knowledge concerning the chemical composition of native SOD, i.e., a metalloglycoprotein having an acetylated N-terminal amino acid and composed of two polypeptide subunits, and the knowledge that bacterially produced proteins are not glycosylated, it was unclear whether SOD produced in bacteria would be active.

Superoxide dismutase is of considerable interest because of its pharmacological properties. Bovine-derived, naturally-occurring superoxide dismutase (orgotein) has been recognized to possess anti-inflammatory properties and is currently marketed in certain European countries, e.g., Spain, for use in the treatment of inflammation. It is also sold in a number of countries including the United States as a veterinary product for treating inflammation, particularly for treating inflamed tendons in horses.

However, supplies of orgotein are limited and prior techniques involving recovery of superoxide dismutase from natural sources such as bovine cells have serious limitations. Furthermore, the orgotein so obtained produces allergic reactions in humans because of its non-human origin.

Additionally, the scientific literature suggests that SOD may be useful in a wide range of clinical applications. These include prevention of oncogenesis and tumor promotion and reduction of cytotoxic and cardiotoxic effects of anti-cancer drugs (Oberley, L. W. and Buettner, G. R., Cancer Research 39, 1141–1149 (1979)); protection of ischemic tissues (McCord, J. M. and Roy, R. S., Can. J. Physiol. Pharma. 60, 1346–1352 (1982)), and protection of spermatozoa (Alvarez, J. G. and Storey, B. T., Biol. Reprod. 28, 1129–1136 (1983)). In addition, there is a great interest in studying the effect of SOD on the aging process (Talmasoff, J. M., Ono, T. and Cutler, R. G., Proc. Natl. Acad. Sci. USA 77, 2777–2782 (1980)).

The exploration of the therapeutic potential of human SOD has been especially limited because of its unavailability.

The present invention provides a method for producing SOD and analogs thereof in bacteria and recovering bacterially produced SOD. It therefore overcomes the problems of unavailability of human SOD and allergic or other adverse reactions in humans caused by SOD of non-human origin, e.g., bovine SOD (orgotein.)

SUMMARY OF THE INVENTION

This invention concerns a plasmid for production of superoxide dismutase or an analog thereof which upon introduction into a suitable bacterial host cell containing the thermolabile repressor $C_I$ renders the host cell capable, upon increasing the temperature of the host cell to a temperature at which the repressor is destroyed, of effecting expression of DNA encoding superoxide dismutase and production of superoxide dismutase comprising:

a double-stranded DNA molecule which comprises in 5' to 3' order the following:

a DNA sequence which contains the promoter and operator $P_L O_L$ from lambda bacteriophage;

the N utilization site for binding antiterminator N protein produced by the host cell;

a DNA sequence which contains a ribosomal binding site for rendering the mRNA of the gene encoding superoxide dismutase capable of binding to ribosomes within the host cell;

an ATG initiation codon;

a restriction enzyme site for inserting the gene encoding superoxide dismutase into the plasmid in phase with the ATG initiation codon; and a gene encoding superoxide dismutase;

and which additionally includes a DNA sequence which contains an origin of replication from a bacterial plasmid capable of autonomous replication in the host cell and a DNA sequence which contains a gene associated with a selectable or identifiable phenotypic trait which is manifested when the plasmid is present in the host cell. A preferred plasmid is pNd-SOD$_{NN}$-12 (ATCC Accession No. 53166).

The plasmids of this invention can be introduced into suitable hosts where the gene encoding superoxide dismutase can be expressed and the superoxide dismutase produced. Suitable hosts include Escherichia coli A1637, A1645, A2602 and A1563; A1645 being presently preferred.

A1637 was obtained from c600 by inserting transposon containing tetracycline resistance gene within the galactose operon as well as the lambda system for expression which is close to galactose operon. c600 is available from the American Type Culture Collection as ATCC Accession No. 23764.

A1645 was obtained from A1637 by selection for Gal$^+$ (ability to ferment galactose) as well as loss of tetracycline resistance. It still contains the lambda expression system but part of the transposon has been removed by selection. Its phenotype is c600 r$^-$m$^+$ gal$^+$ thr$^-$ leu$^-$ Z$^-$ (λcI857ΔH1ΔBAM N+).

Both A1637 and A1645 have been deposited with the American Type Culture Collection in Rockville, Md., U.S.A. containing various plasmids as described more fully hereinafter. All such deposits were made pursuant to the Budapest Treaty on the International Recognition of the Deposit of Microorganisms.

A2602 and A1563 are derived from SA500. Their phenotypes are SA500 his⁻ ilu⁻ gal⁺$^{\Delta}$8($\lambda$c1857$\Delta$H1$\Delta$ BAM N+) and SA500 his⁻ ilu⁻ gal⁺ $\Delta$8 lac ZxA21 ($\lambda$ cI859 int2 xisl nutL3$\Delta$H1), respectively. SA is available from the ATCC as ATCC Accession No. 15746.

The resulting host vector systems can be employed to manufacture superoxide dismutase. The host cells containing the plasmids are grown under suitable conditions permitting production of superoxide dismutase which is then recovered. Presently preferred conditions involve growth at about 42° C. for 10 to 30 minutes, particularly 15 minutes, followed by continued growth at about 37°–39° C. for sufficient time to make the total growth period about 60–90 minutes, particularly growth at 38°–39° C. for about 75 minutes. Presently preferred growth media are lactalbumin hydrolysate with addition of glucose or brain heart infusion.

Using the host vector systems, superoxide dismutase has been prepared. This superoxide dismutase may be incorporated into veterinary or pharmaceutical compositions. This superoxide dismutase directly, or in such compositions, may be used to treat inflammations or to reduce injury caused by oxygen-free radicals, e.g., during reperfusion of a subject following global ischemia or during perfusion of excised isolated organs, e.g., corneas.

GGAATTCC
CCTTAAGG was attached by ligation. The product was cleaved with EcoR1 and inserted into pBR322 which had been cleaved with EcoR1. A clone, pALR1, was isolated which upon cleavage with EcoR1 released a 1200 bp fragment with the sequence:

AATTCTTC ...
GAAG ...

at the 5' end. Formation of this sequence demonstrates that pALR1 contains an EcoR1 restriction site directly adjacent the TTC codon for residue number 1 (phenylalanine) of authentic bGH. pALR1 was subjected to a partial cleavage with Pst1. The digest was ligated with HindIII linkers and cleaved with EcoR1 and HindIII. The fragment containing bGH cDNA was isolated and subcloned into pBR322 between EcoR1 and HindIII restriction sites to give pAL500. The subcloned bGH cDNA fragment was then excised from pAL500 with EcoR1 and HindIII, "filled in" with DNA polymerase "Klenow" fragment and inserted into the pMG100 expression vector (FIG. 1) opened at the BamH1 site and also "filled in" as above. The resulting vector, pREC ⅔, expresses a modified bGH which is altered at its amino terminus as follows:

MetAspGlnPhe¹Pro² ... bGH

The plasmid pREC 2/2 was digested with Pst1 and the fragment containing the $P_L$ promoter and the 5' end of the bGH gene (designated fragment A) was isolated. This fragment was ligated to a Pst1fragment from pAL 500 (designated fragment B). The then resulting vector, pRec ⅔, expresses a modified bGH which is altered at its amino terminus as follows:

MetAspGlnPhe¹Pro² ... bGH

Figure 2:
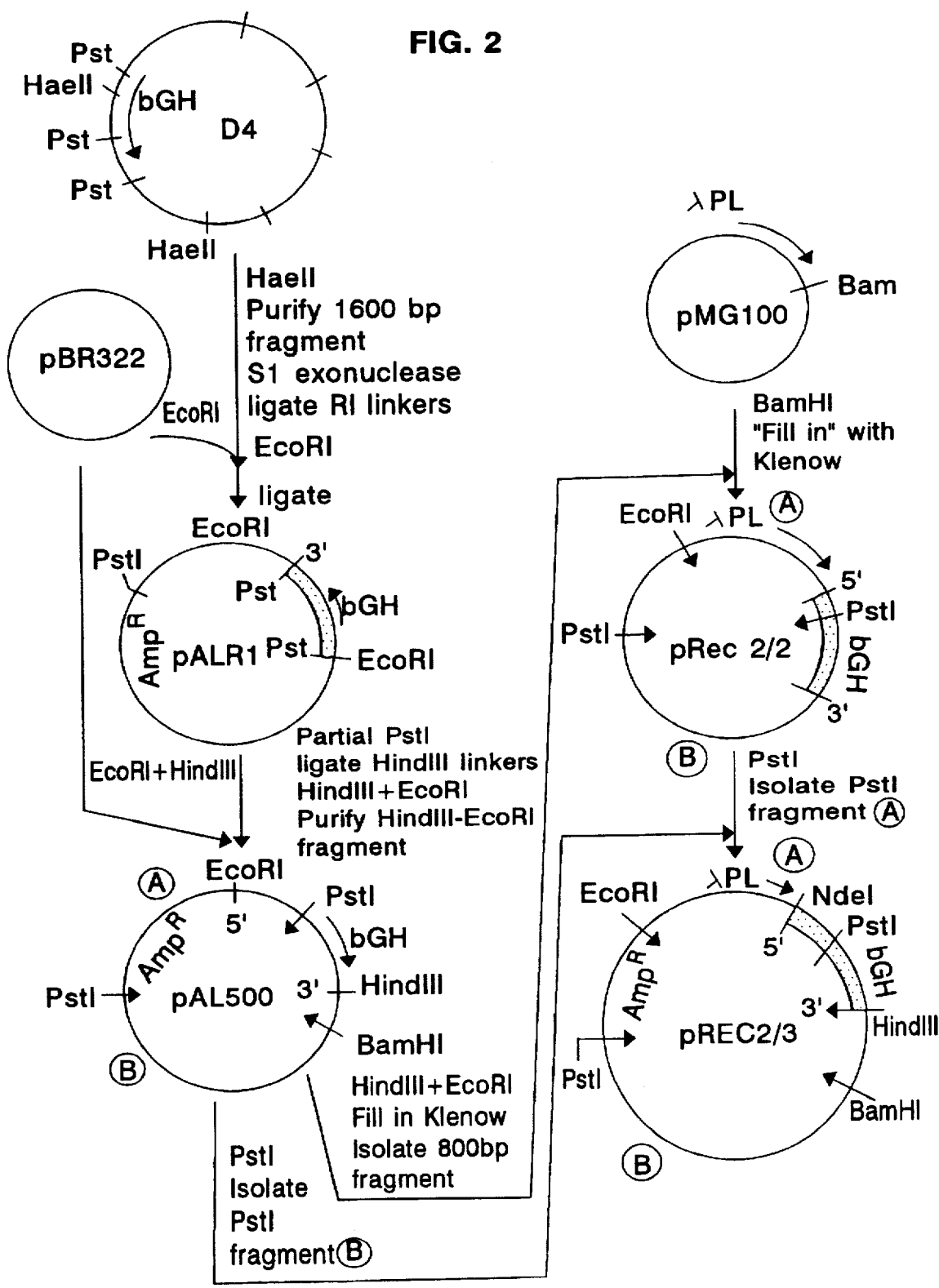
FIG. 2. Construction of pRec ⅔ plasmid. A bGH cDNA containing plasmid, $D_4$, was digested with HaeII. A resulting 1600 bp large fragment was purified and subjected to digestion at 37° C. for 5 minutes with 5 units of S1 exonuclease. A synthetic EcoR1 linker with the sequence.
Figure 3:
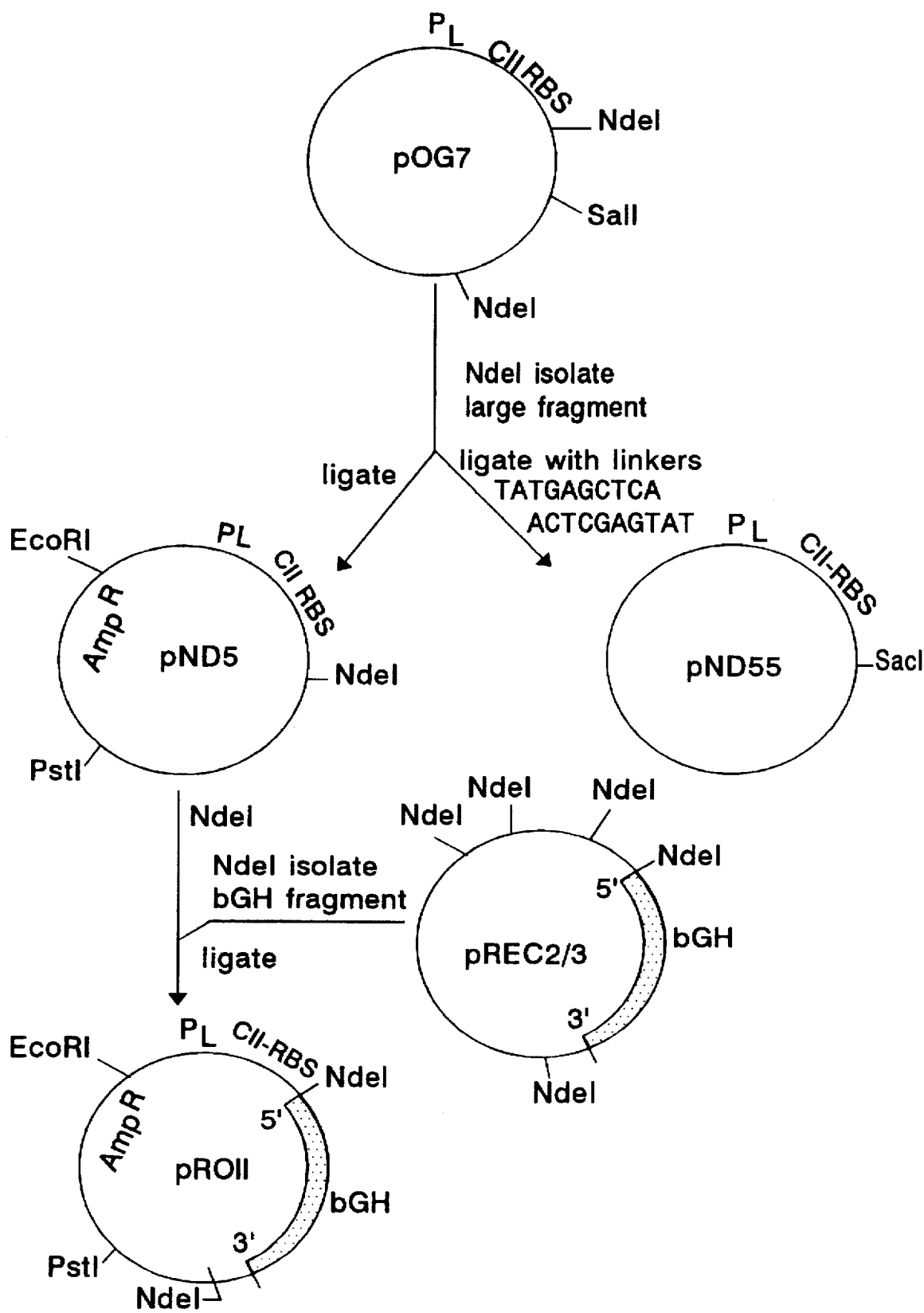

FIG. 3. Construction of expression vectors pND5, pND55 and pRO11. A plasmid pOG7 (A. Oppenheim, S. Gottesman and M. Gottesman, J. Mol. Biol. (1982) 158, 327) was cleaved with Nde1. The ends of the large fragment carrying the $P_L$ promoter $nut_L$, $t_R$ and $C_{II}$-RBS were ligated to give the pND5 expression vector. This pND5 vector DNA is opened with Nde1. Insertion of that Nde1 fragment from pRec ⅔ (FIG. 2) which contains bGH cDNA results in a plasmid pRO11 which appears to be a better expressor of the modified bGH described in FIG. 2 than pRec ⅔. Insertion of synthetic linkers with the sequence:

TATGAGCTCA
ACTCGAGTAT into pOG7 cleaved with Nde1 results in an expression vector pND55 which contains a unique Sac1 restriction site in front of ATG. When pND55 is cleaved with Sac1 and treated with DNA polymerase "Klenow" fragment an ATG initiation codon results which follows the $P_L$ promoter and $C_{II}$-RBS. This vector is suitable for expression of a wide variety of eukaryotic genes lacking an ATG initiation codon.

Figure 4:
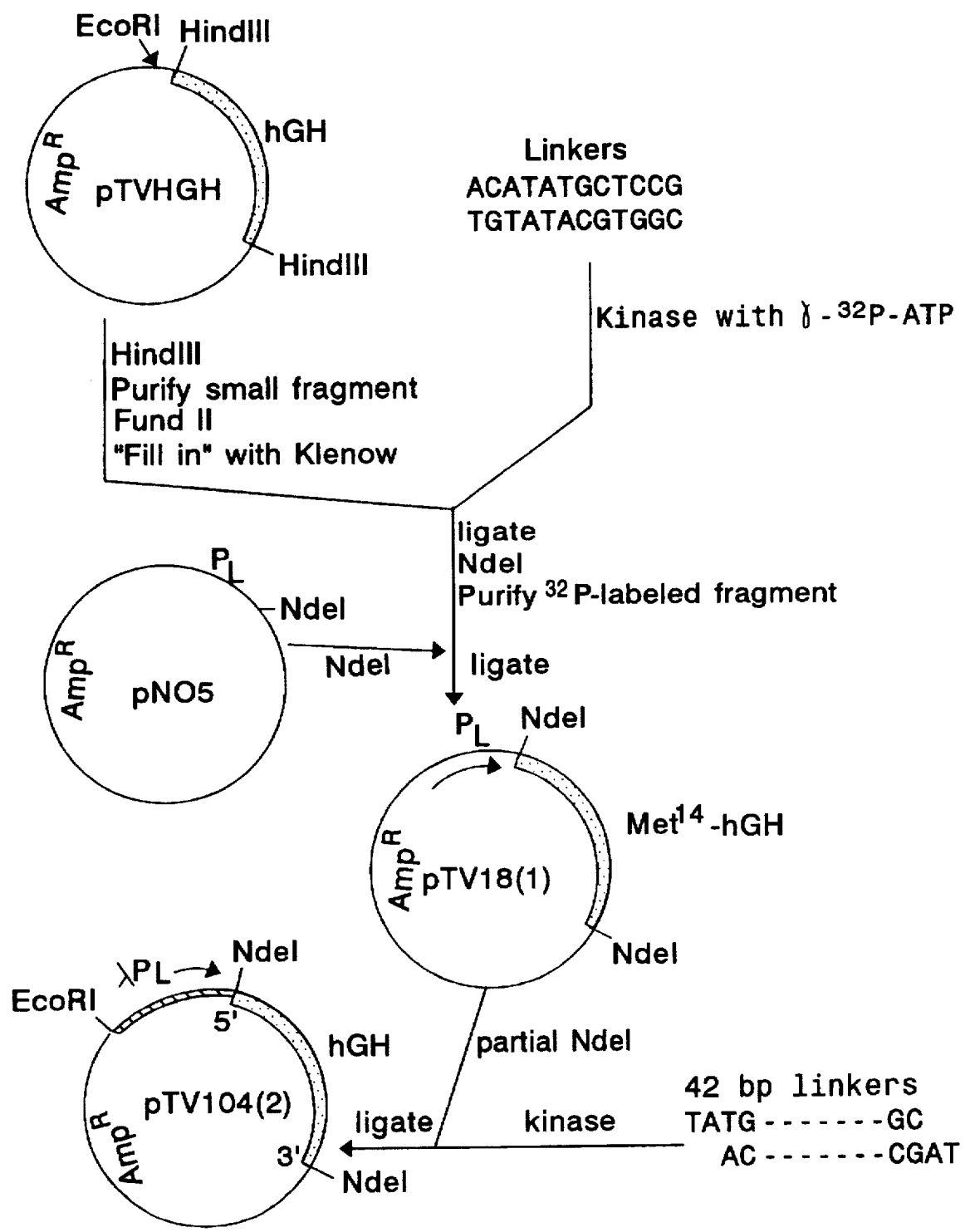

FIG. 4 Construction of pTV 18(1) and pTV 104(2). A plasmid, pTVHGH was prepared by cloning cDNA encoding hGH into the HindIII site of pBR 322 using standard methods. Meth. Enzymol. (1979) 68, 75. This plasmid was digested with HindIII. The resulting 800 base pair fragment was purified and further digested with FnuDII and "filled in" with DNA polymerase "Klenow" fragment. This treatment removes codons for the first 16 amino acids of hGH. The resulting DNA fragment is ligated with a synthetic linker which restores the codons for the sequence of hGH from Met¹⁴ and regenerates an Nde1 restriction site in front of the ATG codon for Met¹⁴. After treatment with Nde1 this semisynthetic DNA was inserted into the pND5 vector opened with Nde1. The resulting plasmid pTV 18(1) expresses hGH under control of the $P_L$ promoter. This hGH is an analog missing the first 13 amino acid residues and having at its N-terminus Met¹⁴.

Plasmid pTV 18(1) was partially digested with Nde1 and ligated with a synthetic linker which contains the codons for amino acids 1–13 of hGH:

T A T G T T C C C A A C C A T T C C A T T A T C -
C C G T C T G T T C G A C A A C G C
A C A A G G G T T G G T A A G G T A A T A G G G C A G A -
C A A G C T G T T G C G A T.

The linker is also complementary to the Nde1 site on pTV 18(1) and positions the complete hGH gene in phase with the ATG initiation codon of the pND5 expression vector (FIG. 3). Thus, the resulting plasmid, pTV 104(2), expresses native hGH with an extra methionine at the N-terminus.

Figure 5:
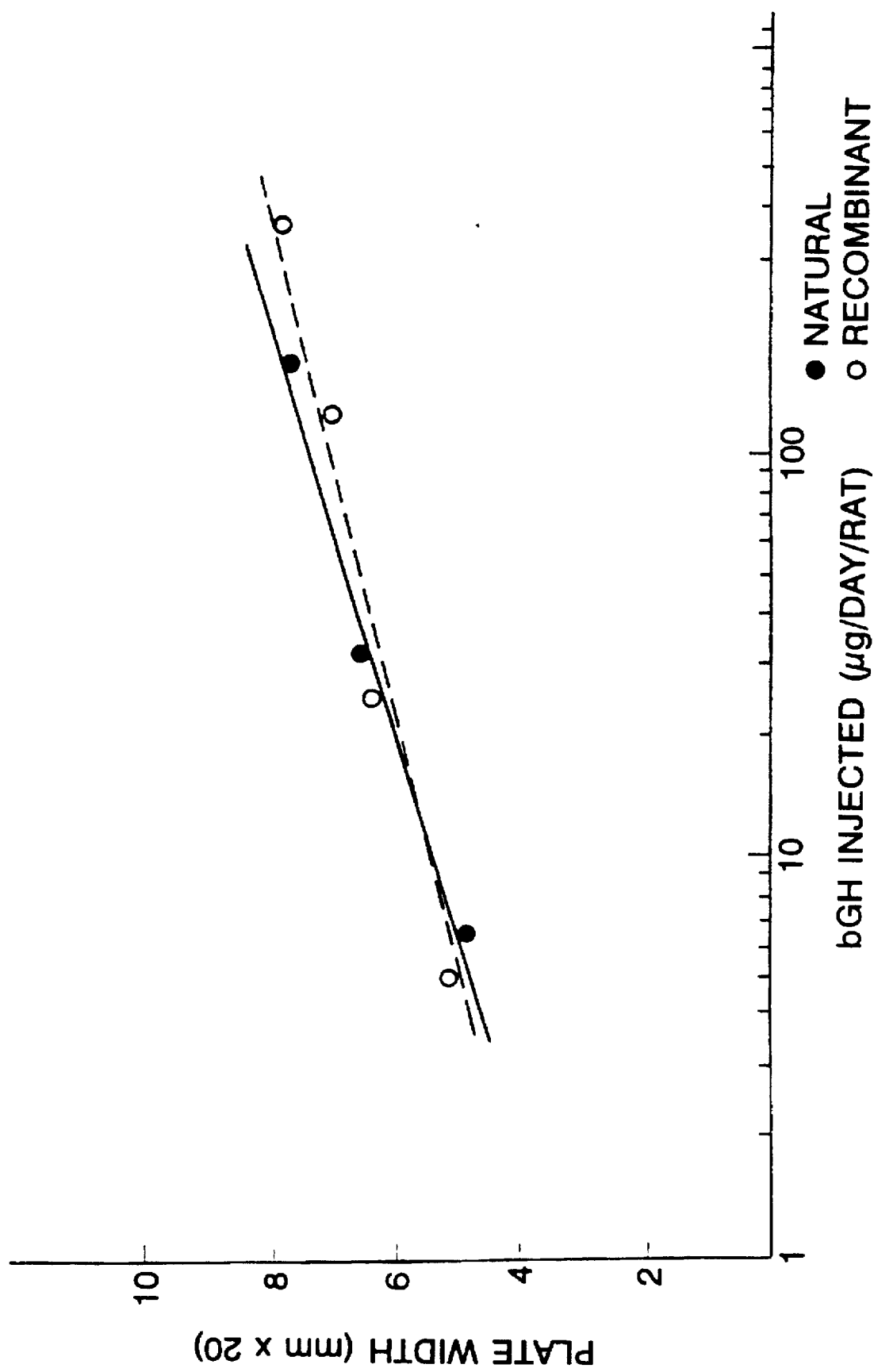

FIG. 5. Tibia test This figure shows the comparison between effect of pRec ⅔ bGH analog and authentic bGH on the bone plate growth of hypophysectomized rats.

FIG. 6. DNA and amino acid sequence of SOD. This figure shows the nucleotide sequence of the coding strand of the double-stranded cDNA molecule which encodes human cytoplasmic superoxide dismutase. It also shows the amino acid sequence of the human superoxide dismutase polypeptide encoded by the cDNA.

Figure 7:
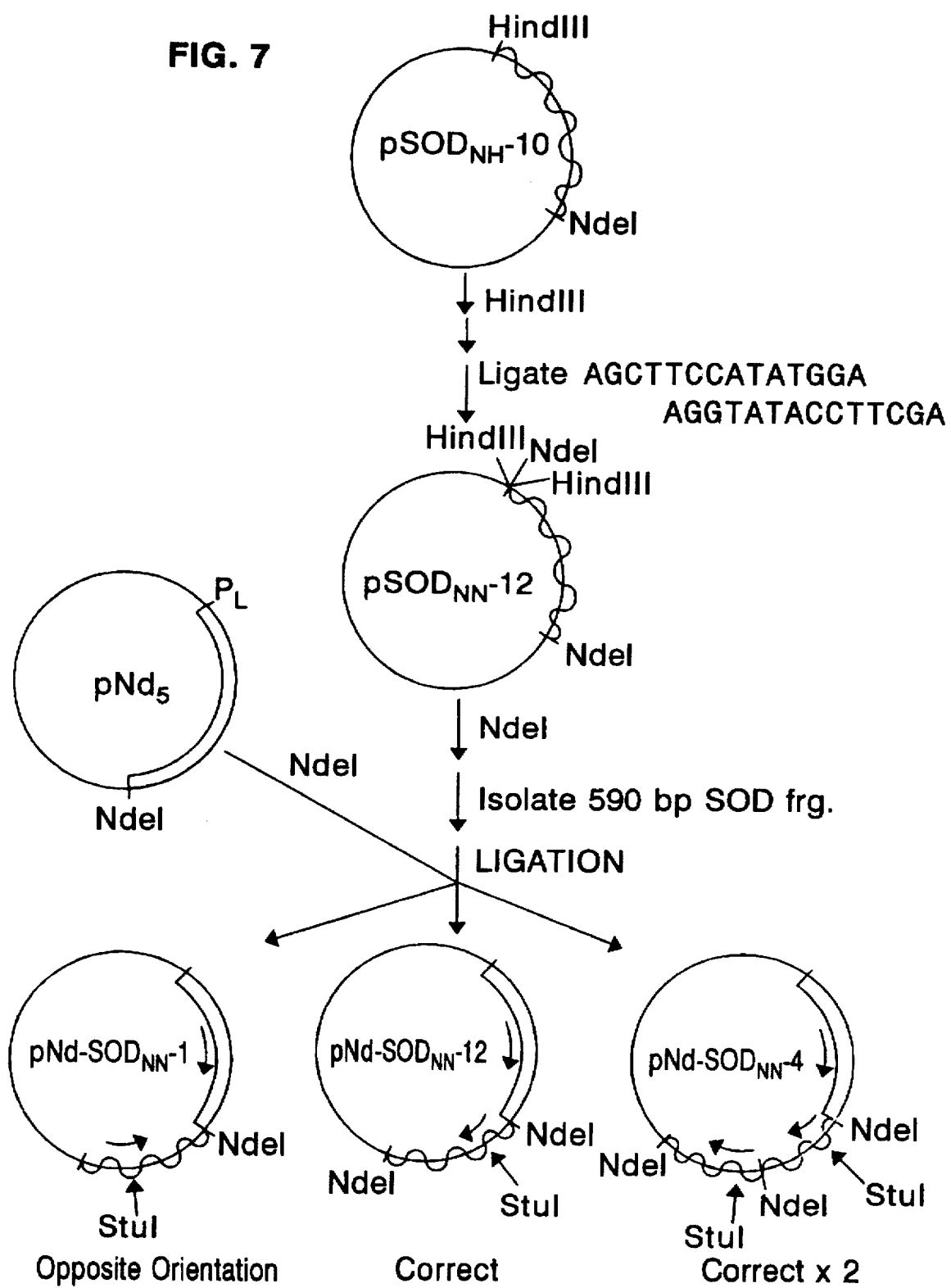

FIG. 7. Construction of pNd-SOD$_{NN}$-12. Plasmid pSODNH–10 was digested with NdeI and treated with 5 units calf intestinal alkaline phosphatase at 37° C. for 30 minutes. The resulting DNA was ligated to a synthetic linker of the sequence:

AGCTTCCATATGGA
AGGTATACCTTCGA to form pSOD$_{NN}$-12. Cleavage of pSOD$_{NN}$-12 with NdeI released a 590 bp SOD cDNA fragment. This fragment was isolated. The pND5 plasmid (see FIG. 3) was cleaved with NdeI, then treated with calf intestinal alkaline phosphatase and ligated to the 590 bp SOD cDNA containing fragment. Transformation of *E. coli* (strain 1645) with the resulting plasmids yielded three types of clones. One of these, designated pNd-SOD$_{NN}$-12, upon growth and induction produces a protein having superoxide dismutase activity. This plasmid, pNd-SOD$_{NN}$-12 has been deposited with the American Type Culture Collection under ATCC Accession No. 53166.

DETAILED DESCRIPTION OF THE INVENTION

A plasmid has been developed which enables the achievement of enhanced levels of gene expression and polypeptide expression. The plasmid is a double-stranded DNA molecule. Upon introduction into a suitable bacterial host cell containing the thermolabile repressor $C_I$ and increasing the temperature of the host to a temperature at which the repressor is destroyed, the plasmid renders the host cell capable of effecting expression of a desired gene inserted into the plasmid and production of the polypeptide encoded by the gene.

The plasmid includes in 5' to 3' order the following:

a DNA sequence which contains the promoter and operator $P_L O_L$ from lambda bacteriophage;

the N utilization site for binding antiterminator N protein produced by the host cell;

a DNA sequence which contains a ribosomal binding site for rendering the mRNA of the desired gene capable of binding to ribosomes within the host cell;

an ATG initiation codon or a DNA sequence which is converted into an ATG initiation codon upon insertion of the desired gene into the vector;

a restriction enzyme site for inserting the desired gene into the vector in phase with the ATG initiation codon; and a gene encoding the desired polypeptide.

The plasmid also includes a DNA sequence which contains an origin of replication from a bacterial plasmid capable of autonomous replication in the host cell and a DNA sequence which contains a gene associated with a selectable or identifiable phenotypic trait which is manifested when the plasmid is present in the host cell.

The host for use with the plasmid is *Escherichia coli*. The presently preferred strains are A1637, A1645, A2602 and A1563. A1637 and A1645 are presently the more preferred strains.

A1637 was obtained from c600 by inserting transposon containing tetracycline resistance gene within the galactose operon as well as the lambda system for expression which is close to galactose operon. c600 is available from the American Type Culture Collection, as ATCC Accession No. 23724.

A1645 was obtained from A1637 by selection for Gal$^+$ (ability to ferment galactose) as well as loss of tetracycline resistance. It still contains the lambda expression system but part of the transposon has been removed by selection. Its phenotype is C600 r$^-$m$^+$ gal$^+$ thr$^-$ leu$^-$ lac Z$^-$ λcI857 Δ H1 ΔBAM N+).

Both A1637 and A1645 have been deposited with the American Type Culture Collection in Rockville, Md., U.S.A. containing various plasmids as described more fully hereinafter. All such deposits were made pursuant to the Budapest Treaty on the International Recognition of the Deposit of Microorganisms.

A2602 and A1563 are derived from SA500. Their phenotypes are SA500 his$^-$ilu$^-$ gal$^+$ Δ8(λcI857 ΔH1Δ BAM N+) and SA500 his$^-$ilu$^-$gal$^+$ Δ8 lac ZxA21(λcI859 int2 xisl nutL 3 ΔH1), respectively. SA is available from the American Type Culture Collection as ATCC Accession No. 15746.

Preferably the plasmid is a covalently closed circular double-stranded molecule. However, it is not essential that the plasmid be covalently closed.

The plasmid achieves its enhanced expression levels after the host cell is heated to a temperature at which the $C_I$ repressor is destroyed. A temperature above about 42° C. is effective for this purpose and since it is desired that unnecessary heat damage to the host cells be avoided to as great an extent as possible, it is generally desirable that the temperature never exceed 42° C. by more than a few degrees.

One important component of the plasmid is the ribosomal binding site. Suitable sites are $C_{II}$ from lambda bacteriophage having the sequence:

TAAGGAAATACTTACAT
ATTCCTTTATGAATGTA;

a synthetic oligonucleotide having the sequence:

TAAGGAAGTACTTACAT
ATTCCTTCATGAATGTA; and the major head protein gene of bacteriophage lambda having the sequence:

TTTTTTTACGGGATTTTTTTATG
AAAAAAATGCCCTAAAAAAATAC.

Another component of the plasmid is the restriction enzyme site for insertion of desired genes into the plasmid in phase with the ATG initiation codon. Numerous such sites may be used. The presently preferred sites are BamH1, Sac1 and Nde1. The most preferred site is Nde1.

The plasmid also includes an origin of replication from a bacterial plasmid capable of autonomous replication in the host cell. Suitable such origins of replication may be obtained from a number of sources. Presently preferred are origins of replication derived from pBR322.

A DNA sequence which contains a gene associated with a selectable or identifiable phenotypic trait which is manifested when the plasmid is present in the host cell is also a component of the plasmid. Suitable genes include those associated with temperature sensitivity or drug resistance, e.g., resistance to ampicillin, chloramphenicol or tetracycline.

Relative to plasmids previously described in the scientific literature, the plasmids of this invention may be used to obtain enhanced expression of a wide variety of genes encoding desirable polypeptide products. Suitable genes include those encoding growth hormones, e.g., bovine, porcine, chicken or human growth hormones; superoxide dismutase; apoprotein E; viral protein 1 of foot and mouth disease virus, protein A from *S. aureus*, interleukin III, enzymes, or analogs of any of the preceding. By analog is meant a polypeptide having the same activity as the naturally occurring polypeptide but having one or more different amino acids at the N-terminus of the polypeptide.

The plasmid may be formed by methods well known to those skilled in the art to which the invention relates. Such methods are described in greater detail in various publications identified herein, the contents of which are hereby incorporated by reference into the present disclosure in order to provide complete information concerning the state of the art.

Figure 1:
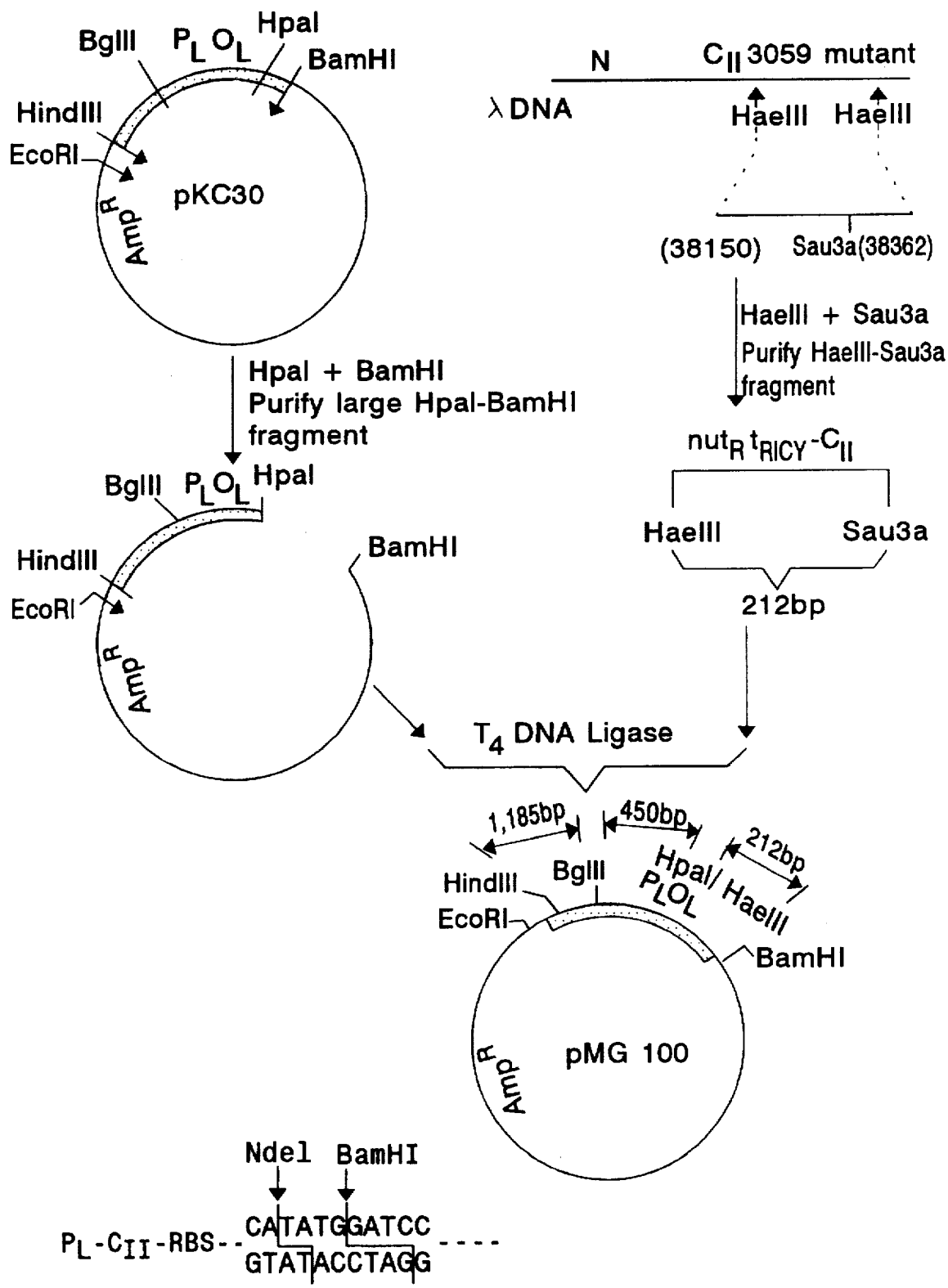
FIG. 1. Construction of pMG100 expression vector. This plasmid was built by inserting a fragment of $\lambda$ phage DNA contained between restriction sites HaeIII (location 38150) and Sau3a (location 38362) into a pKC30 plasmid DNA cleaved with Hpa1 and BamH1. The HaeIII-Sau3a fragment carries $nut_R$, $t_{R1}$, cy⁻ and ribosomal binding site of $C_{II}$ protein ($C_{II}$-RBS). Subcloning of the $C_{II}$-RBS containing DNA into pKC30 creates pMG100 which contains a unique BamH1 restriction site right after the ATG initiation codon of $C_{II}$-RBS and an NdeI restriction site within the ATG triplet (bottom inset). Numbers in parentheses denote location of restriction sites on the $\lambda$ phage DNA.

One presently preferred vector is pMG100 having the restriction map shown in FIG. 1. This vector has had cDNA encoding bovine growth hormone inserted into its BamH1 restriction site. The resulting plasmid is designated pRec ⅔. Its restriction map is shown in FIG. 2. The plasmid pRec ⅔ bGH was introduced into *Escherichia coli* strain A1637 using conventional transformation methods. The resulting host vector system has been-deposited under ATCC Accession No. 39385.

A second presently preferred vector is pND5 having the restriction map shown in FIG. 3. Bovine growth hormone cDNA has been inserted into its Nde1 restriction site. The resulting plasmid is designated pRO11. Its restriction map is also shown in FIG. 3. The plasmid pRO11 was introduced into *E. coli* strain A1637 via transformation. The host vector system which resulted has been deposited under ATCC Accession No. 39390.

The vector pND5 has also been used to clone human growth hormone. One plasmid designated pTV 18(1) and another designated pTV 104(2) have been created by inserting hGH cDNA into the Nde1 restriction sites. pTV 18(1) is shown in FIG. 4. It has been introduced into *E. coli* strain A1637 via transformation. The resulting host vector system has been deposited under ATCC No. 39386. pTV 104(2) is shown in FIG. 4. It also has been introduced into *E. coli* strain A1637. The resulting host vector system has been deposited under ATCC Accession No. 39384.

The vector pND5 has also been used to clone superoxide dismutase (SOD). A plasmid designated pND-SOD$_{NN}$-12 has been created by inserting hSOD cDNA into the Nde1 restriction site. See Proc. Natl. Acad. Sci. USA 79, 2808–2811 (1982) and Proc. Natl. Acad. Sci. USA 80, 5465–5469 (1983). The hSOD cDNA inserted is referred to in pending U.S. patent application Ser. No. 489,786 filed Apr. 29, 1983 and is shown in FIG. 6 of this application. The plasmid pND-SOD$_{NN}$-12 is shown in FIG. 7. It has been introduced into *E. coli* strain A1645 via transformation. The resulting host vector system has been deposited with the American Type Culture Collection under ATCC Accession No. 53166.

Using the same approach other plasmids may be prepared by inserting into the restriction enzyme site of a vector of the invention a gene encoding a desired polypeptide.

The preceding specific host vector systems involve *E. coli* A1637 and A1645. However, as previously indicated other strains have been used including A2606 and A1563. These host vector systems may be used to produce polypeptides such as bovine and human growth hormones and human superoxide dismutase. To do so, the host vector system is grown under suitable conditions permitting production of the polypeptide which is then recovered.

Suitable conditions involve growth of the host vector system for an appropriate period of time at about 42° C. followed by continued growth at about 37°–39° C. for an additional period of time, the growth being carried out on a suitable medium.

Desirably the initial period of growth is about 10 to 30 minutes at 42° C. followed by growth at 37°–39° C. for a sufficient period of time such that the total period of growth is about 60 to 90 minutes. Preferably the growth is for about 15 minutes at 42° C. followed by about 75 minutes at 38°–39° C. Suitable media include lactalbumin hydrolysate with addition of glucose and brain heart infusion. In order to stably maintain the vector in the host it is critical that the host be maintained under selective pressure, e.g., addition of antibiotic.

By means of the preceding method a number of bGH, hGH and SOD analogs have been prepared. These have the activity of the naturally occurring hormones or superoxide dismutases, respectively.

bGH analogs have the activity of natural bGH and an identical amino acid sequence except for variations at the N-terminus of up to five (5) amino acids. Examples include the following:

1) amino acid methionine added to N-terminus of the phenylalanine form of bGH.

2) amino acid methionine added to N-terminus of the alanine form of bGH.

3) amino acid sequence Met-Asp-Pro added to N-terminus of the phenylalanine form of bGH.

4) amino acids up to methionine (4 position) removed from N-terminus of phenylalanine form of bGH.

hGH analogs have the activity of natural hGH and an identical amino acid sequence except for variations at the N-terminus. An example is the following:

1) amino acid methionine added to N-terminus of natural hGH.

Superoxide dismutase having the activity of naturally-occurring SOP has been prepared in bacteria by the preceding method. Examples of bacterially-produced SODs which may be produced by the method of the invention include human superoxide dismutase, Cu-Zn human superoxide dismutase and analogs thereof.

Purified superoxide dismutase or an analog thereof may be recovered from the bacterial cell in which it is produced by the following method.

First, the cell wall of the bacterial cell is disrupted to produce a lysate. This may be accomplished by mechanical or other suitable disruption methods.

Then, the pH of the lysate is adjusted to a neutral pH, e.g. 7.4, so as to precipitate the SOD or analog. Optionally, lysozyme or deoxyribonuclease may be added to the lysate prior to adjusting the pH to a neutral pH. The precipitate is then solubilize d by further adjusting the pH to an alkaline pH, e.g. 11.8, and the SOD or analog separated from other soluble components by gel filtration chromatography.

Finally, the separated SOD or analog is subjected to ion exchange chromatography to concentrate it and purified superoxide dismutase or analog is recovered. Optionally, prior to recovery, the superoxide dismutase or analog may be further concentrated by dialysis followed by lyophilization.

Veterinary compositions may be prepared which contain effective amounts of one or more bGH analogs and a suitable carrier. Such carriers are well-known to those skilled in the art. The analogs may be administered directly or in the form of a composition to a bovine in order to increase milk or meat production.

Pharmaceutical compositions may be prepared which contain effective amounts of one or more hGH analog and a suitable carrier. Such carriers are well-known to those skilled in the art. The analogs may be administered directly or in the form of a composition to a human subject, e.g., one afflicted by dwarfism, to treat deficiencies in hGH production by the subject.

Veterinary and pharmaceutical compositions may also be prepared which contain effective amounts of SOD or one or more SOD analogs and a suitable carrier. Such carriers are well-known to those skilled in the art. The SOD or analog may be administered directly or in the form of a composition to the animal or human subject, e.g., to treat a subject afflicted by inflammations or to reduce injury to the subject by oxygen-free radicals on reperfusion following global ischemia. The SOD or analog may also be added directly or in the form of a composition to the perfusion medium of an isolated organ, e.g., to reduce injury to an isolated organ by oxygen-free radicals on perfusion after excision, thus prolonging the survival period of the organ, e.g. cornea.

EXAMPLES

The examples which follow are set forth to aid in understanding the invention but are not intended to, and should not be so construed as to, limit its scope in any way. The examples do not include detailed descriptions for conventional methods employed in the construction of vectors, the insertion of genes encoding polypeptides of interest into such vectors or the introduction of the resulting plasmids into bacterial hosts. Such methods are well-known to those skilled in the art and are described in numerous publications including the following:

Principles of Gene Manipulation, An Introduction to Genetic Engineering, 2nd Edition, edited by R. W. Old and S. B. Primrose, Univ. of Calif. Press (1981)

Met. Enzymol. vol. 68, Recombinant DNA, edited by Ray Wu

Met. Enzymol. vol. 65, Nucleic Acids (Part 1), edited by Lawrence Grossman and Kivie Moldave T. Maniatis, E. F. Fritsch and J. Sambrook, Molecular Cloning; A Laboratory Manual, Cold Spring Harbor Laboratory, NY (1982)

H. V. Bernard et al., Gene (1979) 5, 59

A. B. Oppenheim et al., J. Mol. Biol. (1982) 158, 327

E. Remaut et al., Gene (1981) 15, 81

Example 1

Expression Vectors

As used herein the term expression vector refers to a group of plasmids useful for expressing desired genes in bacteria, particularly in E. coli. The desired gene may be inserted into the expression vector or alternatively, the promoters on the expression vector may be excised and placed in front of the desired gene.

I. $P_L$ Expression Vectors

A. pMG 100 pMG 100, as shown in FIG. 1 and described in detail under Description of the Figures is composed of λ DNA inserted into the multicopy plasmid pBR322. The salient features of the λ DNA are the λ$P_L$ promoter, N utilization sites L and R (nut$_L$ and nut$_R$) termination R1 site (tri), the $C_{II}$ ribosomal binding site and an ATG initiation codon. Other features are shown in FIG. 1.

pMG100 was prepared from pKC30. pKC30 in turn was prepared by subcloning of λ $P_L$ promoter in the following manner.

λphage DNA was digested with Xho1 and Sma1 restriction endonucleases and the unique fragment comprised of 6393 base pairs was purified and subsequently digested with HindIII and BamH1 restriction endonucleases. The resulting fragment comprised of 2397 base pairs and containing $P_L$ promoter was purified and ligated into a pBR322 DNA large fragment isolated from the HindIII and BamH1 digest. The subclone was identified by colony hybridization, recovered and plasmid DNA isolated.

(Oppenheim, A. et al., J. Mol. Biol. (1982) 158, 327.)

This plasmid and its derivatives containing eukaryotic genes may be maintained in suitable E. coli hosts. The most important feature of the host is that it provides the thermosensitive repressor CI857 and the antitermination N protein. (Gottesman, M. E. et al., J. Mol. Biol. (1978) 140, 197).

This vector has numerous advantages over previously described expression vectors including:

1. Extremely Levels of Expression

This vector is capable of directing expression of foreign proteins in E. coli at levels as high as 15–25% of the total cellular protein.

2. Thermoinducible Regulation of Expression

The $P_L$ promoter is inactive when the CI represor is bound to it. The CI857 repressor is thermosensitive, that is, it binds to the promoter at 30° C. but is inactivated at 42° C. Thus, by increasing the temperature of fermentation to 42° C. the host bacteria are induced to produce the desired protein.

The advantages of such a system include the following:

(a) a foreign protein which is toxic to E. coli can be produced when desired thus avoiding cell death early in the fermentation process.

(b) overproduction of a protein may stabilize it and prevent proteolytic degradation. (Cheng, Y. E. et al., Gene (1981) 14, 121) Thus, "instantaneous" overproduction using a tightly regulated promoter such as $P_L$ may be preferable to continuous low level production.

3. High Copy Number

The $P_L$ promoter in pMG100 is found on a plasmid with a high copy number in distinction to λ itself which is present in low copy numbers in E. coli. This increases expression levels.

4. Ribosome Binding Site and Initiation Codon

This expression vector contains a strong procaryotic ribosomal binding site (RBS) as well as a translation initiation codon (ATG). Thus, any eukaryotic gene may be cloned without the need for adding an initiation codon. Furthermore, the efficient RBS increases levels of expression.

5. Convenient Restriction Site

The expression vector has a BamHI site located directly following the ATG initiation codon which permits proper positioning of the desired gene in order to achieve optimal expression.

6. Nut Site

N protein which is provided by the host binds to Nut site on the expression vector and thereby prevents termination of transcription at the $t_{R1}$ site.

pND5

As shown in FIG. 3, pND5 contains the $P_L$ promoter and the other important components of the expression vectors of this invention. It includes a unique Nde1 site immediately after the ribosomal binding site. The ribosomal binding site differs from the normal $C_{II}$ site. It has the sequence:

TAAGGAAGTACTTACAT
ATTCCTTCATGAATGTA

It may be derived from a mutant or may be chemically synthesized. As described in detail under Description of the Figures pND5 was derived from pOG7. (Oppenheim, A., et al., J. Mol. Biol. (1982) 158, 327) This vector does not contain a translation initiation codon. It appears to provide superior expression of modified bGH and hGH, particularly enhanced yield relative to pMG100 containing a bGH analog.

Example 2

Bovine Growth Hormone

The starting point for bGH cDNA modifications is plasmid D4 which has been described previously. (Keshet, E. et al, Nucleic Acids Research (1981) 9, 19). The D4 plasmid is also described in pending U.S. patent application, Ser. No. 245,943, filed Mar. 20, 1981, claiming priority of Israel patent application, Ser. No. 59,690 filed Mar. 24, 1980. It has previously been deposited with the American Type Culture Collection in an *E. coli* host under ATCC No. 31826.

I. Rec ⅔ bGH

The construction of pRec ⅔ is shown in FIG. 2 and described in the Description of the Figures. bGH cDNA from $D_4$ has been manipulated prior to insertion into PMG100 to provide the correct reading frame.

pRec ⅔ has been introduced into various *E. coli* strains including A1637 by transformation using known methods. A1637 containing pRec ⅔ has been deposited under ATCC No. 39385. This strain produces upon growth an analog of bGH having the amino acid sequence Met-Asp-Gln added to the N-terminus of the phenylalanine form of natural bGH. The amount of bGH analog produced by pRec ⅔ was about 23% of the total protein produced by the bacteria as calculated from scanning of Coomasie stained SDS polyacrylamide gels.

II. pRO11

The construction of pRO11 is shown in FIG. 3 and described in the Description of the Figures. bGH cDNA from $D_4$ was modified and inserted into pNDS5. A fragment of pRec ⅔ was inserted into pND5 to produce pRO11.

pRO11 has been introduced into *E. coli* A1637 by transformation. The resulting host vector system has been deposited under ATCC No. 39390. This strain when grown produces the same analog as pRec ⅔. Preliminary results indicate that pRO11 produces up to 20% more bGH analog than pRec ⅔. The methods used to grow the strain, recover the bGH analog produced and purify it are the same as those described for pRec ⅔ in Example 4.

Example 3

Human Growth Hormone

The starting point for hGH cDNA was cloning of the cDNA from mRNA purified from hypophyses tumor from acromegalic patients into the HindIII site of pBR322.

I. pTV 18(1)

The construction of PTV 18(1) is shown in FIG. 4 and described in the Description of the Figures. hGH cDNA was manipulated prior to insertion into pND5 to provide the correct reading frame.

pTV 18(1) was introduced into *E. coli* A1637 by transformation. The resulting bacteria have been deposited under ATCC No. 39386. This strain upon growth produces an analog of hGH having the sequence of natural hGH beginning with Met[14] and lacking amino acids 1–13. The amount of hGH analog produced by pTV 18(1) was about 8% of the total protein produced by the bacteria.

II. pTV 104(2)

The construction of pTV 104(2) is shown in FIG. 4 and described in the Description of the Figures. hGH cDNA was manipulated prior to insertion into pND5 to provide the correct reading frame.

pTV 104(2) was introduced into *E. coli* A1637 by transformation. The resulting bacteria have been deposited under ATCC No. 39384. This strain upon growth produces an analog of hGH having the sequence of natural hGH preceded by Met at the N-terminus. The amount of hGH analog produced by pTV 104(2) was above 25% of the total protein produced by the bacteria.

Example 4

Growth of pRec ⅔

Stock Cultures

Stock cultures of pRec ⅔ in A1637 are grown on BHI medium (see inoculum), then diluted twofold with 87% glycerol containing phosphate citrate buffer, and stored at −70° C.

Inoculum

Inoculum is propagated in BHI medium (37 g/l brain heart infusion (DIFCO). Sterile medium in shake flask is inoculated from stock culture and incubated 15 hours on shaker at 30° C., 200 r.p.m. Subsequent stages in inoculum propagation are carried out in stirred aerated fermentors. Sterile medium is inoculated with 0.2 ml flask culture per liter, and incubated 15 hours at 30° C., pH ±0.5 with agitation and aeration to maintain dissolved oxygen level above 20% air saturation.

Production

Production medium contains:

| Lactalbumin hydrolysate (enzymatic) | 20 g/l |
|---|---|
| Yeast extract | 10 g/l |
| $K_2HPO_4$ | 2.5 g/l |
| NaCl | 10 g/l |
| Ampicillin | 0.1 g/l |
| Biotin | 0.1 mg/l |
| Thiamine | 1 mg/l |
| Trace elements solution | 3 ml/l |

Ampicillin, biotin and thiamine in solution are filter sterilized separately and added to the sterile production medium before inoculation. Sterile glucose solution is added initially to supply 10 g/l, and during the induction and expression procedure to maintain glucose above 1 g/l Trace elements solution contains:

| $MgSO_4.7H_2O$ | 170 g/l |
|---|---|
| $FeCl_3$ | 16 g/l |
| $ZnCl_2.4H_2O$ | 2 g/l |
| $CoCl_2.6H_2O$ | 2 g/l |
| $Na_2MoO_4.2H_2O$ | 2 g/l |
| $CaCl_2.2H_2O$ | 1 g/l |
| $CuCl_2$ | 1 g/l |
| $H_3BO_3$ | 0.5 g/l |
| Conc. HCl | 100 ml/l |

The medium is inoculated with 5–10% inoculum culture and incubated at 30° C. Agitation-aeration rates are set to maintain dissolved oxygen level above 20% air saturation. The pH is maintained at 7±0.2 with $NH_3$. Once cell concentration reaches about 3 g/l ($OD_{660}$=10) induction is started.

Temperature is raised to 42° C. Maintained there for 15 minutes, then lowered to 38° C. Following incubation at 38°

C. for 1–1½ hours, the culture is chilled, and cells are recovered by centrifugation for hormone purification.

Recovery of bGH

One kilogram of bacterial cells is suspended in 10 volumes of the solution containing 50 mM Tris-Cl (pH 7.4), 50 mM EDTA and 25% sucrose in a Waring blender, with a control of blender's speed to minimize foaming. The homogeneous suspension is continuously passed through a Dynomill cell disruptor (Willy A. Bachofen, Basel) and the homogeneous suspension of disrupted cells is clarified first by centrifugation in a Sharpless centrifuge followed by a continuous centrifugation at 20,000 rpm in a Sorvall centrifuge. The precipitate from both centrifugation steps is collected, washed with 50 mM Tris-Cl (pH 7.4) and resuspended in 500 ml of the same buffer. Lysozyme is added to a final concentration of 2 mg/ml and the suspension is incubated for 1 hour at 37° C. Triton X-100 is then added to a final concentration of 1%, the suspension is cooled to 4° C. and centrifuged at 20,000 rpm for 20 minutes in a Sorvall SS34 rotor. The precipitate is collected, washed twice with 50 mM Tris-Cl, resuspended in 500 ml of 50 mM Tris-Cl (pH 7.4), 5 mM $MgCl_2$ and deoxyribonuclease is added to a final concentration of 20 μg/ml. After incubation for 30 minutes at room temperature the precipitate is collected as above, washed twice with 500 ml of 20 mM Tris-Cl (pH 7.4), 100 mM NaCl and 10 mM EDTA, followed by two washings with 500 ml of distilled water. The precipitate is collected by centrifugation and can be stored at −20° C. for an indefinite time. At this stage the bGH is 80% pure as judged by sodium dodecyl sulfate-gel electrophoresis. The yield is approximately 15 g of bGH.

Purification of bGH

One hundred g of precipitate is suspended in 40 ml distilled water and solubilized by titration with 0.5M NaOH, pH 11.8. The solution is then sonicated for 2 minutes and clarified by centrifugation at 20,000 rpm in a Sorvall SS 34 rotor for 20 minutes. The solution is then applied onto a Sepharose CL-6B column (5×100 cm) equilibrated with 6.5 mM borate buffer, pH 11.8. Column is developed at the rate of 100 ml/hr and fractions of 12 ml are collected. The first peak off the column is discarded. The following two peaks are separated and pooled. The first represents aggregated bGH with low activity; the second bGH with high activity.

A DEAE-Sephacel (25 g/100 gr. equiv. ppt) column is equilibrated with 6.5 mM borate buffer, pH 9.0. The second bGH peak is brought to pH 9.0 with HCl loaded on the DEAE Sephacel column at a rate of 250 ml/hr. The column is washed with 7.5 ml of 6.5 mM borate buffer, pH 9.0, eluted with 6.5 mM borate buffer, pH 9.0 containing 75 mM NaCl. The fractions with $OD_{280}$ above 0.3 are pooled, dialysed against $H_2O$ in Millipore Pellicon dialysis apparatus and then lyophilized.

Example 5

Activity of bGH Analog Produced by pRec ⅔

1. Radioimmunoassay Comparison of bGH Analog with Natural bGH

A solution containing 100 ng/ml bGH analog was prepared in phosphate buffered saline (containing 1% BSA). This solution was diluted serially to concentrations of 50, 25, 12.5, 6.25, 3.12, 1.56 and 0.78 μg/l. Duplicate 0.1 ml aliquots of these solutions were submitted to RIA using a double antibody procedure. The dilution curve was comparable to that obtained with natural bGH.

2. Radioreceptor Binding Assay

A radioreceptor binding assay was performed with rabbit liver membranes as described by T. Tushima and H. G. Freisen (Y. Chin., Endocr. Metab. (1973) 37, 334 using $^{125}$I-hGH as the tracer and authentic bGH solutions for the construction of calibration curves. Samples were incubated in triplicate for two hours at room temperature in 0.3 ml of assay buffer (50 mM Tris, 15 mM $CaCl_2$ and 5 mg/ml bovine serum albumin, pH 7.6). The tubes contained $^{125}$I-hGH (20,000 cpm of preparation of 30–60 μci/μg), 150–250 μg liver membrane protein and either natural bGH (1–100 μg) or extracts of bacterial bGH. The result demonstrated that the bGH activity of the bGH analog is comparable to that of natural bGH.

3. Tibia Test

The bioactivity of the pRec ⅔ bGH analog recovered from engineering bacterial cells according to Example 4 was evaluated by a tibia test. (Parlow, A. F., et al., Endocrinology (1965) 77, 1126.)

Rats were hypophysectomized at 28–30 days of age, then kept for 10–14 days without treatment. Bovine growth hormone derived from bovine pituitaries or from recombinant *E. coli* was dissolved in 0.15M NaCl +0.01M borate, pH 10.0. Rats (4–7 per group) received daily subcutaneous injections of bGH solutions (5–125 μg/day in 0.2 cc) for 5 days while kept on a normal diet (Purina Rat-Chow and water ad-libitum). The animals were sacrificed on the 6th day, their foreleg knee-bones taken out, cut longitudinally, fixed with acetone and stained with 2% $AgNO_3$. The width of the epiphyseal plates was measured by observation through a dissecting binocular (Nikon). Mean values (of 40 readings per rat) were used for the construction of log dose-response curves. Results are shown in FIG. 5.

Example 6

Effect of pRec ⅔ bGH Analog on Lactogenesis in Dairy Cows

The lactogenic effect of bGH has been well documented in the scientific literature in the reports of Bines, J. et al, Brit J. Nutri. (1980) 43, 179 and Peel, C. et al, J. Nutr. (1981) 111, 1662. Bauman, D. et al, J. Dairy Sci. Vol. Supp. 1, Abst 86 (1982) reported that milk production was increased by rDNA bGH. An experiment was conducted to determine the effects of pRec ⅔ bGH on lactogenesis in comparison with natural bGH. Eighteen Holstein cows ranging from 141 to 154 days postpartum were randomly assigned to treatment and blocked according to milk production according to the following design.

| Treatment Groups | Pre-treatment Period | Daily GH Injection |
| --- | --- | --- |
| Control | 5 days | Saline |
| Natural bGH | 5 days | 25 mg/day for 10 days |
| pRec 2/3 bGH | 5 days | 25 mg/day for 10 days |

The bGHs were put in solution with 0.1M $NaHCO_3$ aqueous buffer (pH=8.2) at the concentration of 1 mg/ml immediately prior to each day's injections. The cows were injected with placebo or bGH solution daily for 10 days in a subcutaneous site in the neck region. No injections were given during the 5-day pretreatment period.

The cows were milked twice daily at approximately 6:00 a.m. and 5:00 p.m. Milk weights were recorded by the Boumatic system and recorded in the dairy data system.

The average milk production values for the pre-treatment and bGH treatment periods are shown in Table I. The production level of the control cows was unchanged while the milk volume increased to a similar degree in both the bGH groups. The natural bGH caused an 11.9% increase in milk for a 10-day period and bGH analog treatment resulted in a 10.2% increase. The data were not analyzed for statistical significance due to the small number of animals, however, the magnitudes of the increases are similar to those reported in the literature.

It was concluded that pRec ⅔ bGH stimulates lactogenesis in dairy cows similar to natural bGH.

TABLE I

Bovine Growth Hormone Effect on Lactogenesis
Natural bGH vs pRec 2/3 bGH

| Treatment Group | No. | Av. Daily Milk Production lb/day | | % Increase Over Pretreatment |
|---|---|---|---|---|
| | | Pretreatment 5 days | During GH 10 days | |
| Control | 6 | 57.23 | 57.26 | — |
| Natural bGH 25 mg/day | 5 | 58.54 | 65.50 | 11.9 |
| pRec 2/3 bGH 25 mg/day | 6 | 57.48 | 63.34 | 10.2 |

Each cow was injected subcutaneously with either placebo or bGH solution once daily for 10 days.

Example 7

Superoxide Dismutase (SOD)

The starting point for superoxide dismutase (SOD) cDNA modifications is the plasmid pS61-10 described in Proc. Natl. Acad. Sci., USA, 79:2808 (1982). the SOD cDNA found in the plasmid is also referred to in copending U.S. patent application Ser. No. 489,786, filed on Apr. 29, 1983.

The construction of pNd-SOD$_{NN}$-12 is shown in FIG. 7 and described in the Description of the Figures. The SOD cDNA was modified to introduce an NdeI restriction site at the 5' end of the gene and a Hind III restriction site at the 3' end of the gene. The resulting plasmid, pSOD NH-10, contains SOD cDNA bounded by unique restriction sites.

Expression of SOD, i.e., human Cu/Zn SOD, in *E. coli* was achieved by inserting the further modified cDNA clone into pND5 as shown in FIG. 7. (The plasmid pND5 containing the gene encoding bovine growth hormone and transformed into *E. coli* A1637 has previously been deposited with the American Type Culture Collection under Accession No. 39390.) First, the synthetic linker:

AGCTTCCATATGGA
AGGTATACCTTCGA was inserted into the Hind III site of pSODNH-10, thus generating pSOD$_{NN}$-12 which contains an additional NdeI site. The SOD cDNA bounded by NdeI restriction sites was isolated by cleavage of pSODNN-12 with NdeI and then ligated with pND5 which had been linearized with NdeI. Transformation of *E. coli* strain A1645 yielded 3 different types of clones designated pNd-SOD$_{NN}$-1, 4 and 12 which contain the SOD cDNA insert (see FIG. 7). Clone pNd-SOD$_{NN}$-1 contains the SOD insert in the wrong counterclockwise orientation and therefore serves as a negative control. In clones 4 and 12 the SOD cDNA is positioned in the correct clockwise orientation. Clone 4 contains two tandemly linked SOD genes. Clones 4 and 12 produce upon growth and induction superoxide dismutase which is not glycosylated. The amount of SOD produced by both clones corresponded to about 0.1–0.3% of the total protein produced by the bacteria as calculated from scanning of Coomasie stained SDS-polyacrylamide gels. The pNd-SOD$_{NN}$-12 plasmid was deposited with the American Type Culture Collection under ATCC Accession No. 53166.

Example 8

Growth of pNd-SOD$_{NN}$-12

Stock Cultures

Stock cultures of pNd-SOD$_{NN}$-12 in A1645 are grown on BHI medium (see inoculum), then diluted twofold with 87% glycerol containing phosphate citrate buffer, and stored at −70° C.

Inoculum

Inoculum is propagated in BHI medium (37 g/l brain heart infusion (DIFCO). Sterile medium in shake flask is inoculated from stock culture and incubated 15 hours on shaker at 30° C., 200 r.p.m. Subsequent stages in inoculum propagation are carried out in stirred aerated fermentors. Sterile medium is inoculated with 0.2 ml flask culture per liter, and incubated 15 hours at 30° C. pH 7±0.5 with agitation and aeration to maintain dissolved oxygen level about 20% air saturation.

Production

Production medium contains:

| | |
|---|---|
| Lactalbumin hydrolysate (enzymatic) | 20 g/l |
| Yeast extract | 10 g/l |
| K$_2$HPO$_4$ | 2.5 g/l |
| NaCl | 10 g/l |
| Ampicillin | 0.1 g/l |
| Biotin | 0.1 mg/l |
| Thiamine | 1 mg/l |
| Trace elements solution | 3 ml/l |

Ampicillin, biotin and thiamine in solution are filter sterilized separately and added to the sterile production medium before inoculation. Sterile glucose solution is added initially to supply 10 g/l, and during the induction and expression procedure to maintain glucose above 1 g/l. Trace elements solution contains:

| | |
|---|---|
| MgSO$_4$.7H$_2$O | 170 g/l |
| FeCl$_3$ | 16 g/l |
| ZnCl$_2$.6H$_2$O | 2 g/l |
| CoCl$_2$.6H$_2$O | 2 g/l |
| Na$_2$MoO$_4$.2H$_2$O | 2 g/l |
| CaCl$_2$.2H$_2$O | 1 g/l |
| CuCl$_2$O | 1 g/l |
| H$_3$BO$_3$ | 0.5 g/l |
| Conc. HCl | 100 ml/l |

The medium is inoculated with 5–10% inoculum culture and incubated at 30° C. Agitation-aeration rates are set to maintain a dissolved oxygen level above 20% air saturation. The pH is maintained at 7±0.2 with NH$_3$. Once cell concentration reaches about 3.5 g/l (OD$_{660}$=10) induction is started.

Temperature is raised to 42° C. Maintained there for 15 minutes, then lowered to 38° C. Following incubation at 38° C. for 1–1½ hours, the culture is chilled, and cells are recovered by centrifugation for enzyme purification.

Recovery of SOD

One kilogram of bacterial cells is suspended in 10 volumes of the solution containing 50 mM Tris-Cl (pH 7.4), 50 mM EDTA and 25% sucrose in a Waring blender, with a control of blender's speed to minimize foaming. The homogeneous suspension is continuously passed through a Dynomill cell disruptor (Willy A. Bachofen, Basel) and the homogeneous suspension of disrupted cells is clarified first by centrifugation in a Sharpless centrifuge followed by a continuous centrifugation at 20,000 rpm in a Sorvall centrifuge. The precipitate from both centrifugation steps is collected, washed with 50 mM Tris-Cl (pH 7.4) and resuspended in 500 ml of the same buffer. Lysozyme is added to a final concentration of 2 mg/ml and the suspension is incubated for 1 hour at 37° C. Triton X-100 is then added to a final concentration of 1%, the suspension is cooled to 4° C. and centrifuged at 20,000 rpm for 20 minutes in a Sorvall SS34 rotor. The precipitate is collected, washed twice with 50 mM Tris-Cl, resuspended in 500 ml of 50 mM Tris-Cl (pH 7.4), 5 mM $MgCl_2$ and deoxyribonuclease is added to a final concentration of 20 µg/ml. After incubation for 30 minutes at room temperature the precipitate is collected as above, washed twice with 500 ml of 20 mM Tris-Cl (pH 7.4), 100 mM NaCl and 10 mM EDTA, followed by two washings with 500 ml of distilled water. The precipitate is collected by centrifugation and can be stored at −20° C. for an indefinite time. At this stage the SOD is 80% pure as judged by sodium dodecyl sulfate-gel electrophoresis. The yield is approximately 15 g of SOD.

Purification of SOD

One hundred g of precipitate is suspended in 40 ml distilled water and solubilized by titration with 0.5M NaOH, pH 11.8. The solution is then sonicated for 2 minutes and clarified by centrifugation at 20,000 rpm in a Sorvall SS 34 rotor for 20 minutes. The solution is then applied onto a Sepharose CL-6B column (5×100 cm) equilibrated with 6.5 mM borate buffer, pH 11.8. Column is developed at the rate of 100 ml/hr and fractions of 12 ml are collected. The first peak off the column is discarded. The following two peaks are separated and pooled. The first represents aggregated SOD with low activity; the second SOD with high activity.

A DEAE-Sephacel (25 g/100 gr. equiv. ppt) column is equilibrated with 6.5 mM borate buffer, pH 9.0. The second SOD peak is brought to pH 9.0 with HCl loaded on the DEAE Sephacel column at a rate of 250 ml/hr. The column is washed with 7.5 ml of 6.5 mM borate buffer, pH 9.0, eluted with 6.5 mM borate buffer, pH 9.0 containing 75 mM NaCl. The fractions with $OD_{280}$ above 0.3 are pooled, dialysed against $H_2O$ in Millipore Pellicon dialysis apparatus and then lyophilized.

Example 9

Activity of the SOD Produced by pNd-$SOD_{NN}$-12

The human SOD produced by the expression of pNd-$SOD_{NN}$-12 in *E. coli* A1645 readily reacted with rabbit-anti hSOD antibodies and comigrated with an authentic h SOD on SDS-polyacrylamide gels. Furthermore, if the enzymatic activity of the SOD analog produced by pNd-$SOD_{NN}$-12 is assayed by monitoring the inhibition of reduction of ferricytochrome-c as described by McCord and Fridovich, J. Biol. Chem. (1969), 244: 6049–6055, the results demonstrate that the activity of pNd-$SOD_{NN}$-12 produced SOD is comparable to that of natural human SOD (Sigma) and to that of bovine SOD (Orgotein: Grunenthal GMBH).

What is claimed is:

1. A plasmid for production of superoxide dismutase which upon introduction into a suitable *Escherichia coli* host cell containing the thermolabile repressor $C_1$, renders the host cell capable, upon increasing the temperature of the host cell to a temperature at which the repressor is inactivated, of effecting expression of DNA encoding the superoxide dismutase and production of the superoxide dismutase comprising a double-stranded DNA molecule which comprises in 5' to 3' order the following:

a DNA sequence which contains the promoter and operator $P_LO_L$ from lambda bacteriophage;

the N utilization site for binding antiterminator N protein produced by the host cell;

a DNA sequence which contains a ribosomal binding site for rendering the mRNA of the gene encoding the superoxide dismutase capable of binding to ribosomes within the host cell, wherein the ribosomal binding site is a mutant $C_{II}$ ribosomal binding site from lambda bacteriophage having the sequence:

TAAGGAAGTACTTACAT
ATTCCTTCATGAATGTA;

an ATG initiation codon;

DNA encoding the superoxide dismutase;

and which additionally includes a DNA sequence which contains an origin of replication from a bacterial plasmid capable of autonomous replication in the host cell and a DNA sequence which contains a gene for a selectable or identifiable phenotypic trait which is manifested when the plasmid is present in the host cell.

2. A plasmid of claim 1 designated pNd-$SOD_{NN}$-12, shown in FIG. 7 and deposited under ATCC Accession No. 53166.

* * * * *